US009119777B2

(12) United States Patent
Cook et al.

(10) Patent No.: US 9,119,777 B2
(45) Date of Patent: *Sep. 1, 2015

(54) METHODS AND COMPOSITIONS FOR ADMINISTRATION OF OXYBUTYNIN

(71) Applicant: MICRODOSE THERAPEUTX, INC., Monmouth Junction, NJ (US)

(72) Inventors: Robert Cook, Hillsborough, NJ (US); David A. Byron, Lawrenceville, NJ (US); Scott Fleming, Ewing, NJ (US)

(73) Assignee: MICRODOSE THERAPEUTX, INC., Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/728,706

(22) Filed: Dec. 27, 2012

(65) Prior Publication Data

US 2013/0189319 A1   Jul. 25, 2013

Related U.S. Application Data

(63) Continuation-in-part of application No. 12/904,964, filed on Oct. 14, 2010, now Pat. No. 8,415,390, and a continuation-in-part of application No. 12/130,903, filed on May 30, 2008, now abandoned.

(51) Int. Cl.
*A61K 9/00* (2006.01)
*A61K 31/216* (2006.01)

(52) U.S. Cl.
CPC ............. *A61K 9/0075* (2013.01); *A61K 31/216* (2013.01)

(58) Field of Classification Search
USPC .......................................... 514/534; 424/489
See application file for complete search history.

(56) References Cited

U.S. PATENT DOCUMENTS

| | | | |
|---|---|---|---|
| 2,517,482 A | 8/1950 | Hall | |
| 3,507,277 A | 4/1970 | Altounyan et al. | |
| 3,518,992 A | 7/1970 | Altounyan et al. | |
| 3,635,219 A | 1/1972 | Altounyan et al. | 128/266 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,948,264 A | 4/1976 | Wilke et al. | 128/266 |
| 4,733,797 A | 3/1988 | Haber | 221/8 |
| 5,112,598 A | 5/1992 | Biesalski | 424/46 |
| 5,171,744 A | 12/1992 | Cross et al. | 514/305 |
| 5,344,043 A | 9/1994 | Moulding et al. | 221/71 |
| 5,458,135 A | 10/1995 | Patton et al. | 128/200.14 |
| 5,532,278 A | 7/1996 | Aberg et al. | 514/617 |
| 5,556,611 A | 9/1996 | Biesalski | 424/46 |
| 5,677,346 A | 10/1997 | Aberg et al. | 51/617 |
| 5,694,920 A | 12/1997 | Abrams et al. | 128/200.16 |
| 5,736,577 A | 4/1998 | Aberg et al. | 514/617 |
| 5,814,607 A | 9/1998 | Patton | 514/12 |
| 5,884,624 A | 3/1999 | Barnett et al. | 128/206.24 |
| 5,906,202 A | 5/1999 | Schuster et al. | 128/203.23 |
| 5,998,486 A | 12/1999 | Massaro et al. | 514/725 |
| 6,026,809 A | 2/2000 | Abrams et al. | 128/203.15 |
| 6,183,782 B1 | 2/2001 | Hallworth | 424/497 |
| 6,254,882 B1 | 7/2001 | Jerussi | 424/449 |
| 6,277,890 B1 | 8/2001 | Massaro et al. | 514/725 |
| 6,294,582 B1 | 9/2001 | Jerussi | 514/617 |
| 6,303,648 B1 | 10/2001 | Massaro et al. | 514/461 |
| 6,367,470 B1 | 4/2002 | Denyer et al. | 128/200.14 |
| 6,479,670 B1 | 11/2002 | Belloni et al. | 549/9 |
| 6,492,414 B1 | 12/2002 | Chandraratna et al. | 514/456 |
| 6,528,677 B1 | 3/2003 | Belloni et al. | 560/8 |
| 6,531,460 B1 | 3/2003 | Takenouchi et al. | 514/167 |
| 6,572,893 B2 | 6/2003 | Gordon et al. | 424/489 |
| 6,603,012 B2 | 8/2003 | Belloni et al. | 546/342 |
| 6,629,646 B1 | 10/2003 | Ivri | 239/4 |
| 6,889,690 B2 | 5/2005 | Crowder et al. | 128/203.15 |
| 7,080,644 B2 | 7/2006 | Gumaste | 128/203.21 |
| 7,186,401 B2 | 3/2007 | Keller et al. | 424/43 |
| 7,186,683 B2 | 3/2007 | Henriksen et al. | 514/2 |
| 7,233,228 B2 | 6/2007 | Lintell | 340/309.7 |
| 7,318,434 B2 | 1/2008 | Gumaste et al. | 128/203.15 |
| 7,334,577 B2 | 2/2008 | Gumaste et al. | 128/203.15 |
| 7,538,473 B2 | 5/2009 | Blandino et al. | 310/317 |
| 7,541,349 B2 | 6/2009 | DeLuca et al. | 514/167 |

(Continued)

FOREIGN PATENT DOCUMENTS

| | | | |
|---|---|---|---|
| CA | 2243663 | 7/1997 | |
| CA | 2334590 | 12/1999 | |
| DE | 102005005540 | 8/2006 | ............ A61M 15/00 |
| DE | 102009005048 | 7/2010 | ............ A61H 31/02 |
| EP | 1 499 276 | 1/2005 | ................ A61J 7/00 |
| EP | 0 799 076 | 3/2005 | ............ A62B 18/00 |
| EP | 1 124 602 | 4/2005 | ............ A61M 11/06 |
| EP | 1 534 366 | 6/2005 | ............ A61M 15/00 |
| EP | 1 617 820 | 1/2006 | ............ A61K 47/18 |
| EP | 1 691 781 | 8/2006 | ................ A61J 1/00 |

(Continued)

OTHER PUBLICATIONS

USP 31, Oxybutynin Chloride, Official Monographs/Oxybutynin, p. 1-2, retrieved online Oct. 10, 2013.*

(Continued)

*Primary Examiner* — Brian-Yong Kwon
*Assistant Examiner* — Jennifer A Berrios
(74) *Attorney, Agent, or Firm* — Hayes Soloway P.C.

(57) ABSTRACT

The present invention is directed to methods and compositions for treating pulmonary disease comprising delivering directly to a patient's lungs a therapeutically effective amount of oxybutynin in combination with one or more pharmaceutically effective agents. Oxybutynin may be selected from the group consisting of, but not limited to, a xinafoate salt, a palmitate salt, a pamoic salt, a resonate salt, a laurate salt and other salts. The pharmaceutically effective agents comprise bronchodilators, antiinflammatories, corticosteroids, corticosteroid reversal agent or alveolar growth agents or other agents selected from proteinase or protease inhibitors.

6 Claims, 9 Drawing Sheets

(56) References Cited

U.S. PATENT DOCUMENTS

| | | | | |
|---|---|---|---|---|
| 7,607,435 | B2 | 10/2009 | Lipp | 128/203.13 |
| 7,748,382 | B2 | 7/2010 | Denyer et al. | 128/204.21 |
| 7,915,242 | B2 | 3/2011 | DeLuca et al. | 514/167 |
| 2002/0032409 | A1 | 3/2002 | Ritsche | 604/154 |
| 2002/0179087 | A1* | 12/2002 | Bozung et al. | 128/203.15 |
| 2003/0078294 | A1 | 4/2003 | Chandraratna et al. | 514/456 |
| 2003/0083319 | A1 | 5/2003 | Manchand et al. | 514/167 |
| 2004/0136918 | A1* | 7/2004 | Garrett et al. | 424/46 |
| 2004/0202616 | A1 | 10/2004 | Keller et al. | 424/46 |
| 2004/0250812 | A1 | 12/2004 | Davies et al. | 128/200.14 |
| 2005/0026909 | A1 | 2/2005 | Landau et al. | |
| 2005/0087189 | A1 | 4/2005 | Crockford et al. | |
| 2005/0121027 | A1 | 6/2005 | Nilsson et al. | 128/200.23 |
| 2005/0155601 | A1 | 7/2005 | Steiner et al. | 128/200.23 |
| 2005/0174216 | A1 | 8/2005 | Lintell | 340/309.16 |
| 2005/0209204 | A1 | 9/2005 | Massaro et al. | 514/171 |
| 2005/0267628 | A1 | 12/2005 | Crowder et al. | 700/240 |
| 2006/0011508 | A1 | 1/2006 | Hoegerl et al. | 206/714 |
| 2006/0116425 | A1 | 6/2006 | Massaro et al. | 514/559 |
| 2006/0213503 | A1 | 9/2006 | Borgschulte et al. | 128/200.14 |
| 2006/0257327 | A1 | 11/2006 | Zierenberg et al. | 424/46 |
| 2006/0293261 | A1 | 12/2006 | Takayama | 514/29 |
| 2007/0060652 | A1 | 3/2007 | Fraser et al. | |
| 2007/0137645 | A1 | 6/2007 | Eason et al. | 128/203.15 |
| 2008/0057129 | A1 | 3/2008 | Lerner et al. | 424/489 |
| 2008/0125489 | A1 | 5/2008 | Massaro et al. | 514/559 |
| 2008/0280860 | A1 | 11/2008 | Panina | 514/167 |
| 2008/0299207 | A1* | 12/2008 | Martin | 424/489 |
| 2009/0020113 | A1 | 1/2009 | Watanabe | 128/200.14 |
| 2009/0054382 | A1 | 2/2009 | Ray et al. | 514/171 |
| 2009/0215734 | A1 | 8/2009 | Gerhart | 514/171 |
| 2009/0308390 | A1 | 12/2009 | Smutney et al. | 128/203.15 |
| 2010/0139654 | A1 | 6/2010 | Thoemmes et al. | 128/203.15 |
| 2010/0209536 | A1 | 8/2010 | Weiss et al. | 424/641 |
| 2010/0252032 | A1 | 10/2010 | Thoemmes et al. | 128/200.23 |
| 2010/0294278 | A1 | 11/2010 | Mosier et al. | 128/203.14 |
| 2011/0000481 | A1 | 1/2011 | Gumaste et al. | 128/200.23 |
| 2011/0041844 | A1 | 2/2011 | Dunne | 128/203.12 |
| 2011/0081301 | A1* | 4/2011 | Brambilla | 424/45 |
| 2011/0162642 | A1 | 7/2011 | Akouka et al. | |
| 2011/0253133 | A1* | 10/2011 | Martin et al. | 128/200.23 |
| 2011/0262547 | A1 | 10/2011 | Musa et al. | 424/493 |
| 2012/0077786 | A1 | 3/2012 | Byron et al. | 514/167 |

FOREIGN PATENT DOCUMENTS

| | | | |
|---|---|---|---|
| EP | 1 713 530 | 10/2006 | A61B 5/08 |
| EP | 1 986 721 | 11/2008 | A61M 15/00 |
| EP | 1 581 291 | 1/2009 | A61M 15/00 |
| EP | 2 054 167 | 5/2009 | B06B 1/02 |
| EP | 1 292 347 | 10/2009 | A61M 15/00 |
| EP | 1 691 783 | 11/2009 | A61K 9/14 |
| EP | 2 162 174 | 3/2010 | A61M 15/00 |
| EP | 2 016 965 | 5/2010 | A61M 11/00 |
| EP | 2 047 881 | 8/2010 | A61M 15/00 |
| EP | 2 234 728 | 10/2010 | A61M 15/00 |
| EP | 1 706 099 | 5/2011 | A61K 9/14 |
| WO | WO 00/71108 | 11/2000 | A61K 31/00 |
| WO | WO 03/039464 | 5/2003 | A61K 31/00 |
| WO | WO 03/092576 | 11/2003 | A61J 7/04 |
| WO | WO 2004/002394 | 1/2004 | |
| WO | WO 2004/039763 | 5/2004 | C07C 219/20 |
| WO | WO 2004/093848 | 11/2004 | A61K 9/16 |
| WO | WO 2005/053646 | 6/2005 | A61K 9/14 |
| WO | WO 2005/074455 | 8/2005 | |
| WO | WO 2006/047427 | 5/2006 | A61K 31/216 |
| WO | WO 2007/096111 | 8/2007 | A61M 15/00 |
| WO | WO 2008/021281 | 2/2008 | |
| WO | WO 2008/087437 | 7/2008 | A61K 31/4439 |
| WO | WO 2009/007068 | 1/2009 | A61M 15/00 |
| WO | WO 2009/090084 | 7/2009 | A61M 15/00 |
| WO | WO2011048379 | 4/2011 | A61K 9/12 |
| WO | WO 2011/160932 | 12/2011 | A61M 15/00 |
| WO | WO 2011/163272 | 12/2011 | A61M 15/00 |

OTHER PUBLICATIONS

Patent Examination Report issued in corresponding Australian Patent Application Serial No. 2008259864, dated Apr. 3, 2013 (4 pgs).
Australian Patent Examination Report No. 1, Patent Appln. No. 2008259864, dated Nov. 19, 2012 (4 pgs).
Banerjee et al. "Vitamin D and glucocorticoids differentially modulate chemokine expression in human airway smooth muscle cells" British Journal of Pharmacology vol. 155, 2008 pp. 84-92.
Barnes "Mechanisms in COPD Differences from Asthma" Chest vol. 117, 2000 pp. 10S-14S.
Beer "Development of weekly high-dose calcitriol based therapy for prostate cancer" Urologic Oncology: Seminars and Original Investigations vol. 21, 2003 pp. 399-405.
Chung et al. "Multifaceted mechanisms in COPD: inflammation, immunity, and tissue repair and destruction" European Respiratory Journal vol. 31 No. 6, 2008 pp. 1334-1356.
Damera et al. "Vitamin D Attenuates Growth Factor—Induced Human Airway Smooth Muscle Cell Proliferation" American Journal of Respiratory and Critical Care Medicine vol. 179, 2009 A5606.
Damera, G. et al., "Vitamin D inhibits growth of human airway smooth muscle cells through growth factor-induced phosphorylation of retinoblastoma protein and checkpoint kinase 1", British Journal of Pharmacology (2009), 158, 1429-1441.
Davila et al., "A Short-Term, Multicenter, Randomized Double-Blind Dose Titration Study of the Efficacy and Anticholinergic Side Effects of Transdermal Compared to Immediate Release Oral Oxybutynin Treatment of Patients with Urge Urinary Incontinence," The Journal of Urology, vol. 166, 140-145, Jul. 2001.
Dirami et al. "Lung retinol storing cells synthesize and secrete retinoic acid, an inducer of alveolus formation" American Journal of Physiological Lung Cell Molecular Physiological 2004 pp. L249-L256.
International Search Report & Written Opinion issued in PCT/US11/053513 on Mar. 22, 2012, 9 pgs.
Kunisaki et al. "Vitamin D Levels and Risk of Acute Exacerbations of Chronic Obstructive Pulmonary Disease" American Journal of Respiratory Critical Care Medicine vol. 185 Issue 3, Feb. 1, 2012 pp. 286-290.
Maden et al. "Retionic acid in alveolar development, maintenance and regeneration" The Royal Society vol. 359, Apr. 2004 pp. 799-808.
Massaro et al. "Retinoic acid treatment abrogates elastase-induced pulmonary emphysema in rats" Nature Medicine vol. 3 No. 6, Jun. 1997 pp. 675-677.
Meshi et al. "Emphysematous Lung Destruction by Cigarette Smoke—The Effects of Latent Adenoviral Infection on the Lung Inflammatory Response" American Journal of Respiratory Cell Molecular Biology vol. 26, 2002 pp. 52-57.
Michel et al. "1,25-(OH)$_2$—vitamin D$_3$ and calcipotriol induce IL-10 receptor gene expression in human epidermal cells" Inflammation Research vol. 46, 1997 pp. 32-34.
Mora et al. "Vitamin effects on the immune system: vitamins A and D take centre stage" Nature Reviews Immunology vol. 8, Sep. 2008 pp. 685-698.
Oki et al., "Advantages for Transdermal over Oral Oxybutynin to Treat Overactive Bladder: Muscarinic Receptor Binding, Plasma Drug Concentration, and Salivary Secretion," The Journal of Pharmacology and Experimental Therapeutics, vol. 316, No. 3, pp. 1137-1145, 2006.
Quint "The neutrophil in chronic obstructive pulmonary disease" Journal of Allergy and Clinical Immunology vol. 119 No. 5, May 2007 pp. 1065-1071.
Roth et al. "Feasibility of Retinoids for the Treatment of Emphysema Study" Chest vol. 130, 2006 pp. 1334-1345.
Sakurai "1α,25(OH)$_2$ D$_3$ and its 3-epimer promote rat lunch alveaolar epithelial-mesenchymal interactions and inhibit lipofibroblast apoptosis" American Journal Physiological Lung Cell Molecular Physiology vol. 297, 2009 pp. L496-L505.
Sandhu et al. "The role of vitamin D in asthma" Annals of Allergy, Asthma and Immunology vol. 105, Sep. 2010 pp. 191-199.

(56) References Cited

OTHER PUBLICATIONS

Searing et al. "Decreased serum vitamin D levels in children with asthma are associated with increased corticosteroid use" Journal of Allergy and Clinical Immunology vol. 125 No. 5, May 2010 pp. 995-1000.
Shaheen et al. "Vitamin D and Chronic Obstructive Pulmonary Disease: Justified Optimism or False Hope?" American Journal of Respiratory and Critical Care Medicine vol. 185 Issue 3, Feb. 1, 2012 pp. 239-241.
Shibakura et al. "Simultaneous induction of matrix metalloproteinase-9 and interleukin 8 by all-trans retinoic acid in human PL-21 and NB4 myeloid leukaemia cells" British Journal of Haematology vol. 118, 2002 pp. 419-425.
Staskin, David R., "Transdermal Systems for Overactive Bladder: Principles and Practice," Reviews in Urology, vol. 5, Suppl. 8, pp. S26-S30, 2003.
Supplementary European Search Report and Search Opinion, dated May 10, 2010, (7 pgs).
Sutherland et al. "Vitamin D Levels, Lung Function, and Steroid Response in Adult Asthma" American Journal of Respiratory and Critical Care Medicine vol. 181, 2010 pp. 699-704.
U.S. Official Action dated in related parent U.S. Appl. No. 12/130,903 dated Jun. 3, 2011 (8 pgs).
Xystrakis et al. "Reversing the defective induction of IL-10-secreting regulatory T cells in glucocorticoid-resistant asthma patients" The Journal of Clinical Investigation vol. 116 No. 1, Jan. 2006 pp. 146-155.
Advair Diskus Drug Information, downloaded from www.rxlist.com/advair-diskus-drug.htm (4 pgs).
Side Effects of Veramyst, downloaded from www.rxlist.com/veramyst-side-effects-drug-center.htm (5 pgs).
Food and Drug Administration, Substance Registration System, Standard Operating Procedure, "Substance Definition Manual," Version 5c, Jun. 10, 2007 (94 pgs).
Jashnani et al., "Dry powder aerosol generation in different environments: Performance comparisons of albuterol, albuterol sulfate, albuterol adipate and albuterol stearate," International Journal of Pharmaceutics, Mar. 15, 1996, vol. 130, No. 1, pp. 13-24, Abstract Only (1 pg).
"Monograph Naming Policy for Salt Drug Substances in Drug Products and Compounded Preparations," downloaded from www.drugfuture.com on Feb. 20, 2013 (2 pgs).
Verbeeck et al., "Generic substitution: the use of medicinal products containing different salts and implications for safety and efficacy," European Journal of Pharmaceutical Sciences, May 2006, vol. 28 (14 pgs).
Newman, A., "An Overview of Solid Form Screening During Drug Development," Seventh Street Development Group, May 18, 2011 (60 pgs).
Merritt et al., "Implementing quality by design in pharmaceutical salt selection: a modeling approach to understanding disproportionation," Pharmaceutical Research, Jan. 2013, vol. 30, No. 1, pp. 203-217, Abstract only (1 pg).
Slide presentation on CRO, "Salt Screening—the SFS approach," received Dec. 18, 2012 (1 pg).
European Office Action issued in application No. 08769938.5, dated Jan. 31, 2013 (6 pgs).
International Search Report and Written Opinion issued in related application No. PCT/US2013/074759, dated Apr. 14, 2014 (9 pgs).
Korean Office Action (with translation of relevant portions) issued in related application No. 10-2009-7025995, dated Apr. 14, 2014 (17 pgs).
Notice of Allowance issued in related U.S. Appl. No. 13/830,431, dated Apr. 2, 2014 (17 pgs).
Official Action issued in corresponding Canadian Patent Appln. Serial No. 2,688,542 dated Mar. 5, 2014 (3 pgs).
Korean Office Action issued in application No. 10-2014-7034785, dated Feb. 3, 2015 (21 pgs).
South Korean Notice of Final Rejection Appln. No. 10-2009-7025995, with English translation dated Oct. 27, 2014 (9 pgs).
Canadian Office Action issued in related application No. 2,859,004, dated Sep. 4, 2014 (2 pgs).
Canadian Office Action issued in application No. 2,688,542, dated Jan. 15, 2015 (3 pgs).
Canadian Office Action issued in application No. 2,859,004, dated Jul. 2, 2015 (3 pgs).
International Preliminary Report on Patentability issued in application No. PCT/US2013/074759, dated Jul. 9, 2015 (7 pgs).
Notice of Final Rejection issued in corresponding South Korean Appln. Serial No. 10-2014-7034785 dated Apr. 7, 2015, with English translation (7 pgs).
Office Action issued in related U.S. Appl. No. 14/707,787, dated Jun. 19, 2015 (34 pgs).

\* cited by examiner

Figure 5: 1H NMR of Oxybutynin Xinafoate

Figure 6: FT-IR of Oxybutynin Xinafoate

Figure 9: DSC of Oxybutynin Xinafoate

METHODS AND COMPOSITIONS FOR ADMINISTRATION OF OXYBUTYNIN

CROSS REFERENCE TO RELATED APPLICATION

This application is a continuation in part of co-pending U.S. patent application Ser. No. 12/904,964 filed Oct. 14, 2010, which is a continuation in part of U.S. patent application Ser. No. 12/130,903, filed May 30, 2008 (abandoned).

BACKGROUND OF THE INVENTION

1. Field of the Invention

The present invention relates generally to novel methods of administering oxybutynin, to novel forms of oxybutynin and novel dosage forms containing oxybutynin designed for delivery via the pulmonary route. More specifically, the present invention comprises novel forms of oxybutynin in combination with one or more pharmaceutically effective agents. The invention will be described in particular in connection with pulmonary delivery of oxybutynin for treatment of respiratory diseases such as asthma and chronic obstructive pulmonary disease (COPD), although other uses such as prophylactic, therapeutic or ameliorative treatment of incontinence and intestinal hypermotility, i.e. irritable bowel syndrome, also are contemplated.

2. Description of the Prior Art

Oxybutynin is a racemic compound of the chemical formula 4-diethylaminobut-2-butynyl phenylcyclohexyl-glycolate:

Oxybutynin is an anticholinergic medication that traditionally has been used to treat urinary incontinence, urge incontinence, frequency and over-active bladder symptoms of incontinence (hereinafter singly and collectively referred to as "urge urinary incontinence"). Oxybutynin acts by decreasing muscle spasms of the bladder. It competitively antagonizes the M1, M2, and M3 subtypes of the muscarinic acetylcholine receptor. It also has weaker direct spasmolytic effects on bladder smooth muscle as a calcium antagonist and local anesthetic, but at concentrations far above those used clinically. It is available orally in generic formulation and as the chloride salt, and as the brand-names DITROPAN® and DITROPAN XL®, and as a transdermal product as a patch under the brand-name OXYTROL® or as a gel under the brand name GELNIQUE™.

Oxybutynin currently is administered in oral formulation as a tablet or multiple tablets and a syrup, or transdermally as a patch or topical gel for treating urge urinary incontinence. However, oral delivery of a therapeutically active amount of oxybutynin suffers from a number of disadvantages:

(1) Oxybutynin administered in an oral formulation is absorbed from the intestinal track at an undesirably slow and uneven rate with a variable metabolism that leads to undesirable variations in blood levels and undesirably high dosage rates to achieve a therapeutic response leading to undesirable side effects;

(2) Oxybutynin administered in an oral formulation does not produce desirably high blood levels in a desirably short period of time;

(3) Oxybutynin administered in an oral formation may result in a significant amount not reaching targeted tissues because it is being wasted by metabolism or excretion;

(4) Oxybutynin administered in an oral formation is contraindicated for patients with gastrointestinal obstruction disorders because of the risk of urinary retention; and (5) Oxybutynin administered in oral formulation requires chronic dosing with significant and severe side effects, including dry mouth (xerostomia), constipation, mydriasis, blurred vision, drowsiness, nausea, palpitations, tachycardia and dizziness.

(6) Oxybutynin administered in the oral formulation is subject to first pass metabolism, resulting in the formation of metabolite N-desethyloxybutynin (DEO) which has been attributed to cause the majority of the aforementioned side effects.

As a result, many patients discontinue oral anticholinergic therapy. These adverse effects have been associated with relatively high levels of oxybutynin's primary metabolite, DEO, which circulates in concentrations approximately 4 (oxybutynin ER) to 10 (oxybutynin IR) times that of the parent compound. DEO has been shown to have a greater affinity and binding duration at receptors in the salivary glands than does oxybutynin. In other words, the metabolite DEO has shown to have a higher side effect-to-efficacy ratio than the parent compound oxybutynin. Levels of DEO in oral and transdermal therapy have been reported to be approximately 10-40 ng/mL and 3 ng/mL, respectively. To completely eliminate the side effect concerns of this drug, it would be advantageous to decrease the DEO levels in systemic circulation to below those found in current therapies (i.e. below 3 ng/mL).

Moreover, there are other disadvantages to current oral administration of oxybutynin, including:

(7) Oxybutynin administered in an oral formation is administered as a tablet or multiple tablets which may lack the desirable ease of administration because some people may dislike the swallowing of tablets, or may have difficulty swallowing tablets, or are unable to swallow tablets, or may require a liquid to assist swallowing of tablets; and (8) Oxybutynin-containing tablets also contain several inactive ingredients, including significant amounts of lactose, corn starch, magnesium silicate, magnesium stearate, and talc which may be considered undesirable because some people may dislike or be allergic to one or more of these inactive ingredients that comprise the oxybutynin tablets.

Transdermal delivery of oxybutynin has many of the aforesaid disadvantages. Additionally, some patients suffer skin irritation from transdermal patches, have difficulty maintaining and tolerating patch-to-skin contact, or dislike the aesthetics of a transdermal patch.

Bronchoconstriction, a hallmark of pulmonary disease such chronic obstructive pulmonary disease and asthma, involves the narrowing of air passages (bronchi and bronchioles) in the lungs due to muscle contraction. Often times the muscle contraction is a result of activation of muscarinic receptors on the membranes of smooth muscle cells. This results in the limitation of air flowing to and from the lung and causes shortness of breath and overall difficulty in breathing.

Pulmonary disease includes, but is not limited to, acute bronchitis, acute respiratory distress syndrome (ARDS), asbestosis, asthma, atelectasis, aspergilliosis, bronchiectasis, bronchiolitis, bronchopulmonary dysplasia, byssinosis, chronic bronchitis, coccidiomycosis, chronic obstructive pulmonary disease (COPD), cystic fibrosis, emphysema, eosinophilic pneumonia, hantavirus pulmonary syndrome, histoplasmosis, human metapneumovirus, hypersensitivity pneumonitis, influenza, lung cancer, lymphangiomatosis, mesothelioma, necrotizing pneumonia, nontuberculosis Mycobacterium, pertussis, pleural effusion, pneumoconiosis, pneumonia, primary ciliary dyskinesia, primary pulmonary hypertension, pulmonary arterial hypertension, pulmonary fibrosis, pulmonary vascular disease, respiratory syncytial virus, sarcoidosis, severe acute respiratory syndrome, silicosis, sleep apnea, sudden infant death syndrome, and tuberculosis. The most common lung diseases generally comprise asthma, bronchitis, COPD, emphysema, and pneumonia.

Of all pulmonary diseases, the most prevalent appears to be COPD. According to the World Health Organization estimates in the year 2004, 64 million people had COPD and 3 million people died of COPD. WHO predicts that COPD will become the third leading cause of death worldwide by 2030. The Merck Manual (2011) provides that an estimated 12 million people in the US have COPD and describes COPD as the 4th leading cause of death, resulting in 122,000 deaths in 2003 compared with 52,193 deaths in 1980. From 1980 to 2000, the COPD mortality rate increased 64% (from 40.7 to 66.9/100,000). Prevalence, incidence, and mortality rates increase with age and though prevalence is higher in men, total mortality is similar in both sexes. Incidence and mortality are generally higher in caucasians, blue-collar workers, and people with fewer years of formal education, probably because these groups have a higher prevalence of smoking. COPD is increasing worldwide because of the increase in smoking in developing countries, the reduction in mortality due to infectious diseases, and the widespread use of biomass fuels.

Current therapeutic agents for COPD predominately comprise bronchodilators administered via inhalation, including inhaled long-acting beta$_2$-agonists (LABA) or long acting muscarinic antagonists (LAMA). Although oxybutynin is a LAMA, no effective pharmaceutical form, or method of administration has heretofore been developed to treat COPD using oxybutynin. Many diseases of the respiratory tract are known to respond to treatment by the direct application of therapeutic agents. As these agents are most readily available in dry powdered form, their application is most conveniently accomplished by inhaling the powdered material through the nose or mouth. This powdered form can result in the better utilization of the medicament in that the drug is deposited exactly at the site desired and where its action may be required; hence, very minute doses of the drug are often equally as efficacious as larger doses administered by other means, with a consequent marked reduction in the incidence of undesired side effects and medicament cost. In addition, a drug in dry powder form may be used for treatment of diseases other than those of the respiratory or pulmonary system. When the drug is deposited on the very large surface areas of the lungs, it may be very rapidly absorbed into the blood stream; hence, this method of application may take the place of administration by injection, tablet, or other conventional means.

Although some forms of oxybutynin hydrochloride compositions have been contemplated for administration in dry powder form, no such forms have yet been successfully reduced to practice. There remains a need for oxybutynin therapeutic compositions that are clinically effective and having the appropriate physiochemical properties.

Thus, there is a need for improved delivery of oxybutynin, which will provide enhanced bioavailability, minimized variations in blood levels, and achieve more rapid onset of activity, as compared to oral dosage or transdermal dosage forms, while at the same time providing relative ease of administration and reduced side effects compared to current oral and transdermal delivery methods for administering oxybutynin.

SUMMARY OF THE INVENTION

The foregoing and other objects of the invention are achieved by providing methods and compositions for pulmonary delivery of oxybutynin to a mammalian host, particularly a human patient, whereby to provide for rapid absorption of oxybutynin while avoiding the above and other disadvantages of oral and transdermal administration. More specifically, the present invention relates to novel dosage forms and compositions of oxybutynin for treating pulmonary and respiratory diseases, including but not limited to, chronic obstructive pulmonary disease and asthma. In certain embodiments, the present invention is also related to improving underlying physiological dysfunction contributing to pulmonary disease. The present invention provides effective administration of therapeutic agents to specific airways of the lungs by utilizing controlled site delivery.

More particularly, it has been discovered herein that oxybutynin-containing compositions can be usefully administered to mammals by pulmonary delivery at lower dosage levels to elicit a therapeutic response with a marked reduction in systemic metabolites. It is understood that the major contributor to the untoward effects of oxybutynin therapy is systemic levels of the metabolite, DEO. An increased contribution of DEO toward side effects is due to its greater affinity toward receptors in non-targeted tissues, i.e. salivary glands. In addition, this invention can provide enhanced bioavailability, achieve more rapid onset of activity, and ease of administration, as compared to conventional oral and transdermal methods of administration, for treating urinary incontinence. Pulmonary delivery of oxybutynin provides relief for treating respiratory diseases such as chronic obstructive pulmonary disease (COPD) and asthma, as well as relief for treating both urinary incontinence and for treating stress urinary incontinence, as well as intestinal hypermotility, i.e. irritable bowel syndrome. The present invention also provides novel forms of oxybutynin as well as novel dosage forms and treatment protocols for administering oxybutynin.

BRIEF DESCRIPTION OF THE DRAWINGS

Further features and advantages of the present invention will be seen from the following detailed description, taken in conjunction with accompanying drawings, in which.

DETAILED DESCRIPTION OF PREFERRED EMBODIMENTS

The present invention may be understood more readily by reference to the following detailed description of the specific embodiments included herein. Reference is made to the accompanying drawings, which form a part hereof, and in which is shown, by way of illustration, various embodiments of the present disclosure. Although the present invention has been described with reference to specific details of certain embodiments thereof, it is not intended that such details should be regarded as limitations upon the scope of the invention. The entire text of the references mentioned herein are hereby incorporated in their entireties by reference including U.S. patent application Ser. No. 12/904,964 filed Oct. 14, 2010, and application Ser. No. 12/130,903, filed May 30, 2008. Also incorporated by reference is U.S. patent application Ser. No. 13/246,686 filed Sep. 27, 2011.

Pulmonary delivery of oxybutynin to the respiratory tract can be used advantageously to treat respiratory disease, urge urinary incontinence and symptoms of stress urinary incontinence. Unlike conventional oral and transdermal delivery of oxybutynin which require chronic dosing with significant side effects and require hours to reach therapeutically active blood levels, dry powder pulmonary delivery of oxybutynin permits a patient to enjoy relief at significantly lower doses with concomitant reduction in side effects such as dry mouth. Dry powder pulmonary delivery of oxybutynin also permits a patient to enjoy relief from symptoms of stress urinary incontinence on a more immediate or as-needed basis. Similarly, dry powder pulmonary delivery of oxybutynin permits a patient to achieve prophylactic relief from symptoms of respiratory distress or on an as needed basis.

A feature and advantage of the present invention that results from pulmonary delivery of oxybutynin is that the typical primary metabolite formation of DEO is largely avoided as are the adverse side effects resulting therefrom as above mentioned.

Figure 1:
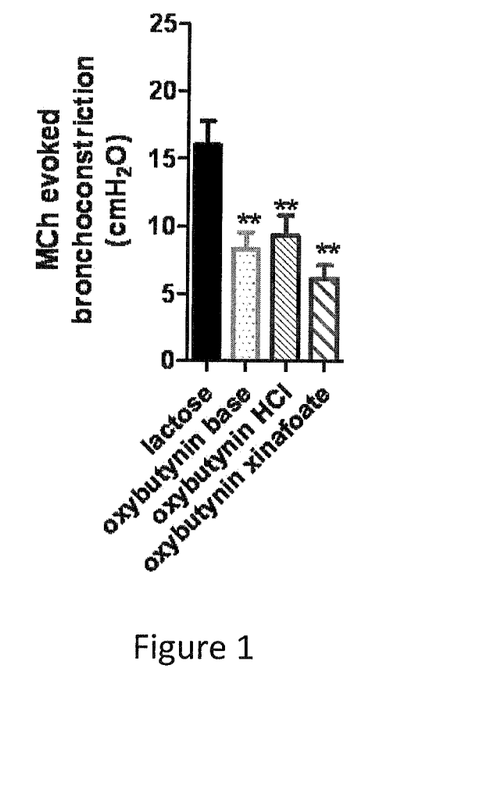
FIG. 1 plots inhibition of methacholine induced bronchoconstriction of oxybutynin and oxybutynin salts at 18 hours. More particularly, changes in bronchoconstriction for oxybutynin treated animals were compared the time matched lactose control animals using ANOVA followed by Dunnetts test. ** P<0.01.

Additionally, we have found that certain salts of oxybutynin, when administered via pulmonary delivery result in a significantly longer acting efficacy effect than anticipated given that the oral half life is only 2.5 hours. These salts include a novel salt form of oxybutynin, namely the xinafoate salt of oxybutynin which heretofore has not been reported in the literature. For example, all dosing of oxybutynin is typically three times daily due to a relatively short half-life of 2.5 hours with minimal plateau levels of drug remaining at approximately eight (8) hours. On the other hand, pulmonary delivery of a salt of oxybutynin unexpectedly provides a duration of activity in guinea pig lungs of up to 18 hours which would translate into one to twice daily human dosing. This is illustrated in FIG. 1 attached.

The xinafoate salt of oxybutynin is prepared by reacting oxybutynin with xinafoic acid in methyl tert-butyl ether under an inert (nitrogen) atmosphere. Other salts of oxybutynin that advantageously can be administered by pulmonary delivery include palmitate, pamoic, resinate, laurate and stearate salts and also esters of oxybutnin, and can provide unexpected results of improved half-life as well as reduced adverse metabolite production.

In selecting a preferred configuration of oxybutyin for therapeutic administration, the inventors herein contemplated several properties of various oxybutynin salts, including but not limited to the following:

Solubility→PK, bioavailability, and changes in dissolution rate.
Surface energy→aerosolization (dispersibility), physical stability (of particles)
Hydration state→stability, solubility
Kinetics of degradation→stability
Crystal hardness→micronization, physical stability
Hygroscopicity→handling, stability
Dissolution
Melting point
Dosage form to be developed
Route of administration
Loading in dosage form
Toxicology of counterions, especially pulmonary toxicology As a free base, oxybutynin is poorly soluble and lipophilic, having an aqueous solubility and Log P of 0.01 mg/mL and 3.3, respectively. To improve drug solubility, oral oxybutynin was formulated as a hydrochloride salt, improving the gastric solubility to 20 mg/mL (measured at pH 4) (see U.S. Pat. No. 6,087,396). For the purposes of pulmonary delivery, the inventors herein developed an alternate strategy where a less soluble, more lipophilic salt form was engineered. It has been noted previously that a slow dissolution rate and potential for lipophilic binding in vivo may prolong drug retention in the lung and delay absorption into systemic circulation. The corticosteroids triamcinolone acetonide and fluticasone propionate have shown mean absorption times in the lungs of 2.9 hours and 5-7 hours, respectively (Patton (2007) Nature Reviews in Drug Discovers, V6, p 67-74). To increase the potential for lung retention, the xinafoic acid (xinofoate) salt of oxybutynin was synthesized. Other lipophilic salts, such as stearates and palmitates were attempted; however, it was experimentally determined that the thermodynamic driving force indicated by the difference in pKa of oxybutynin and xinafoic acid (8.24 vs. 2.7) would more likely result in salt formation.

Before conducting salt synthesis studies, the solubility of oxybutynin in various organic solvents was evaluated (Table 1). These solubility studies indicated a number of potential solvents to use during salt synthesis; however, only methyl tert-butyl ether (MTBE) produced crystalline salt and acceptable yields. The synthesis and crystallization methods were adapted from a method used to synthesize oxybutynin hydrochloride (U.S. Pat. No. 6,140,529). In the patented method, ethanol is added to MTBE to precipitate salt crystals; however, since the xinafoate salt is likely much less soluble than the hydrochloride, water was used to induce precipitation of oxybutynin xinafoate. The results and specifications of all salt synthesis experiments are summarized in Table 2. Example 3 provides a description of the process used for synthesizing oxybutynin xinafoate salt.

TABLE 1

Oxybutynin Solubility in Various Organic Solvents

| Solvent | Solvent Class | Oxybutynin Wt (mg) | Solvent Volumes | Temp (° C.) | Result |
|---|---|---|---|---|---|
| THF | II | 20.4 | 5 | 23 | Soluble |
| Methyl THF | II | 18.4 | 5 | 23 | Soluble |
| i-PrOAc | III | 20.7 | 5 | 23 | Soluble |
| EtOAc | III | 19.5 | 5 | 23 | Soluble |
| MTBE | III | 21.7 | 5 | 30 | Soluble; No recrystallization |
| Toluene | II | 22.0 | 5 | 23 | Soluble |
| Ethanol | III | 21.9 | 5 | 31 | Soluble; No recrystallization |
| 2-Propanol | III | 20.8 | 5 | 39 | Soluble; No recrystallization |
| Acetone | III | 20.8 | 5 | 23 | Soluble |
| Methanol | II | 18.1 | 5 | 23 | Soluble |

Preferred embodiments of the present invention comprise methods and compositions for treating pulmonary disease comprising delivering directly to a patient's lungs a therapeutically effective amount of oxybutynin in combination with one or more pharmaceutically effective agents. In certain embodiments, the oxybutynin and the pharmaceutically effective agent(s) are delivered in dry powder form. The dry powder oxybutynin may be selected from the group consisting of, but not limited to, a xinafoate salt, a palmitate salt, a pamoic salt, a resonate salt, a laurate salt and other salts. Pharmaceutically effective agents comprise bronchodilators, antiinflammatories, corticosteroids, corticosteroid reversal (CR) agents, alveolar growth agents or other agents selected from proteinase or protease inhibitors.

In certain preferred embodiments, the bronchodilators comprise long-acting and short-acting beta agonists and derivatives or pharmaceutically acceptable salts thereof. The anti-inflammatories may include inhaled corticosteroids, phosphodiesterase inhibitors or leukotriene receptor antagonists. Furthermore, the corticosteroids may comprise budesonide, fluticasone, beclomethasone, flunisolide, mometasone, triamcinolone, ciclesonide, loteprednol, fluorometholone, and derivatives or pharmaceutically acceptable salts thereof.

Alternative embodiments may optionally comprise corticosteroid reversal agent comprising vitamin D, synthetic vitamin D, vitamin D analogs, vitamin D receptor agonists, vitamin D receptor partial agonists, calcitriol, antioxidants, iNOS inhibitors, Phosphoinositide-3-kinase-.delta. inhibitors, p38 MAP kinase inhibitors, JNK inhibitors, MIF inhibitors, low-dose theophylline, p-glycoprotein inhibitors, macrolides, calcineurin inhibitors, statins, and equivalents thereof. In addition, the alveolar growth agents may comprise vitamin A, All Trans Retinoic Acid (ATRA), retinoic acid receptor (RAR)

TABLE 2

Salt Synthesis Experiments

| Entry (scale) | Acid (equiv) | Solvent (1) (vol) | Solvent (2) (vol) | Temp (° C.) | Isolation | % Recovery | Comments |
|---|---|---|---|---|---|---|---|
| 1 (0.5 g) | Xinafoic (1) | MTBE (3 vol) | EtOH (4) | 45 | Evaporation | 94 | Foam; 1:1 salt by NMR; 1.2% residual EtOH |
| 2 (0.5 g) | Xinafoic (1) | MTBE (3 vol) | MTBE (5.4) | 50 | Cooled to 5° C.; then evaporated | 92 | Foam; 1:1 salt by NMR; 3% residual MTBE |
| 3 (0.5 g) | Xinafoic (1) | i-ProAc (6 vol) | none | 50 | Cooled to 5° C.; then evaporated | 101 | Oil; 1:1 salt by NMR; 5.5% residual IPAc |
| 4 (0.5 g) | Xinafoic (1) | 2-PrOH (10 vol) | none | 80 | Evaporated | 86 | Oil; 1:1 salt by NMR |
| 5 (0.5 g) | Xinafoic (1) | Methyl THP (10 vol) | none | 80 | Evaporated | 106 | Oil; 1:1 salt by NMR |
| 6 (0.5 g) | Xinafoic (1) | Toluene (10 vol) | none | 80 | Evaporated | 112 | Oil; 1:1 salt by NMR |
| 7 (0.5 g) | Xinafoic (1) | MIBK (10 vol) | none | 80 | Evaporated | 118 | Oil; 1:1 salt by NMR |
| 8 (0.5 g) | Xinafoic (1) | Water (10 vol) | 2-PrOH (10) | 80 | Evaporated | 99 | Oil; 1:1 salt by NMR |
| 9 (3 g) | Xinafoic (1) | MTBE (3 vol) | EtOH (4) | 50 | Crystallized | 77 | 1:1 salt: 0.16% residual MTBE; Crystalline by XRPD; DSC: 104-106° C. |
| 10 (3 g) | Xinafoic (1) | MTBE (5 vol) | none | 50 | Crystallized | 89 | 1:1 salt: 0.23% residual MTBE; Crystalline by XRPD; DSC: 104-106° C. |
| 11 (20 g) | Xinafoic (1) | MTBE (5 vol) | none | 50 | Crystallized | 89 | 1:1 salt by NMR; 0.27% residual MTBE; 0.057% residual H$_2$O (KF) | agonists and RAR selective alveolar growth agents, RAR selective agonists, palovarotene and equivalents thereof.

In preferred embodiments, the present invention comprises methods and compositions for treating pulmonary disease comprising delivering directly to a patient's lungs a therapeutically effective amount of oxybutynin in combination with a LABA wherein the oxybutynin is present in the form of oxybutynin xinofoate and the LABA is selected from the group including, but not limited to, formoterol, salmeterol, odalaterol, carmoterol, vilanterol.

In alternatively preferred embodiments, the present invention comprises methods and compositions for treating pulmonary disease comprising delivering directly to a patient's lungs a therapeutically effective amount of oxybutynin in combination with a LABA wherein the oxybutynin is present in the form of oxybutynin xinofoate and the LABA is selected from the group including, but not limited to, formoterol, salmeterol, odalaterol, carmoterol, vilanterol and further comprising an inhaled corticosteroid (ICS) wherein the ICS comprises budesonide, fluticasone, mometasone, or additionally, a selective agent selected from the 'soft steroid' class, for instance, ciclesonide or loteprednol.

In alternatively preferred embodiments, the present invention comprises methods and compositions for treating pulmonary disease comprising delivering directly to a patient's lungs a therapeutically effective amount of oxybutynin in combination with a LABA, and further comprising a CR reversal agent wherein the oxybutynin is present in the form of oxybutynin xinofoate, the LABA is selected from the group including, but not limited to, formoterol, salmeterol, odalaterol, carmoterol, vilanterol and the CR reversal agent is selected from the group including, but not limited to, vitamin D, vitamin D analogs, synthetic vitamin D, vitamin D receptor agonists and antagonists, calcitol and equivalents thereof.

In alternatively preferred embodiments, the present invention comprises methods and compositions for treating pulmonary disease comprising delivering directly to a patient's lungs a therapeutically effective amount of oxybutynin in combination with a LABA, a CR reversal agent, and further comprising an ICS, wherein the oxybutynin is present in the form of oxybutynin xinofoate; the LABA is selected from the group including, but not limited to, formoterol, salmeterol, odalaterol, carmoterol, vilanterol; the CR reversal agent is selected from the group including, but not limited to, vitamin D, vitamin D analogs, synthetic vitamin D, vitamin D receptor agonists and antagonists, calcitol and equivalents thereof; and the ICS is selected from the group including, but not limited to, budesonide, fluticasone, mometasone, or additionally, a selective agent selected from the 'soft steroid' class.

In alternatively preferred embodiments, the present invention comprises methods and compositions for treating pulmonary disease comprising delivering directly to a patient's lungs a therapeutically effective amount of oxybutynin in combination with a LABA, an alveolar growth agent, wherein the LABA comprises formoterol and the alveolar growth agent is selected from the group including, but not limited to, ATRA, cis-retionoic acid and palovarotene.

The above embodiments may be delivered using a dry powder inhaler (DPI), a DPI comprising a piezo vibrator, metered dose inhaler (MDI) or liquid nebulizer. In addition, the therapeutic compositions of the above-described embodiments may be delivered in dry powder form having a mass median aerodynamic particle size selected from the group consisting of 0.5-20 microns, 0.5-15 microns, 0.5-10 microns, or 0.5-5 microns. The dosages of the therapeutically effective amount of oxybutynin in combination with one or more pharmaceutically effective agents is within the range of 0.001 to 20 mg per day, 0.02 to 15 mg per day, or 0.05 to 10 mg per day administered as needed.

TERMS AND DEFINITIONS

As used herein, the term "oxybutynin" is intended to encompass not only oxybutynin as an anhydrous powder, but any salt or derivative of oxybutynin having antispasmodic, anticholinergic activity like oxybutynin, and which is non-toxic and pharmacologically acceptable, for example, oxybutynin xinafoate or oxybutynin hydrochloride. Other suitable salts include but are not limited to the palmitate, pamoic, resonate and laurate salts.

"An effective amount," as used herein, is an amount of the pharmaceutical composition that is effective for treating pulmonary disease, urinary incontinence or irritable bowel syndrome i.e., an amount of oxybutynin of a defined aerodynamic particle size suitable for absorption in the lungs, that is able to reduce or eliminate the symptoms of COPD, asthma, urinary and stress incontinence.

"A pharmaceutical composition," as used herein, means a medicament for use in treating a mammal that comprises oxybutynin in a dry powder form of a defined aerodynamic particle size prepared in a manner that is suitable for pulmonary administration to a mammal. A pharmaceutical composition according to the invention may also, but does not of necessity, include a non-toxic pharmaceutically acceptable carrier.

"A defined aerodynamic particle size," as used herein, means particles having a size sufficiently small so as to be delivered to the lungs. For optimal delivery to the lungs, the dry powder form of the oxybutynin preferably should be micronized or spray dried to a mass median aerodynamic diameter powder size of 0.05-20 microns, 0.5-15 microns, 0.5-10 microns, or 0.5-5 microns. However, other methods for producing controlled size particles, e.g. supercritical fluid processes, controlled precipitation, etc., also advantageously may be employed.

"A therapeutically effective amount" as used herein will vary with the age, weight and general physical condition of the individual, frequency of dosing, severity of COPD, asthma, incontinence, and whether urge or stress incontinence, or irritable bowel syndrome is being treated. Generally for treating respiratory diseases, a therapeutically effective amount will comprise the active ingredient in a quantity of from 0.001 to 20 mg per day, 0.02 to 15 mg per day, or 0.05 to 10 mg per day, administered as needed. Generally, for treating urge incontinence, a therapeutically effective amount will comprise the active ingredient in a quantity of from 1 to 20 mg/day, preferably 1 to 10 mg/day. The active ingredient may be given once a day. Preferably, however, the active ingredient will be administered in smaller doses two or three or more times a day to maintain more consistent plasma levels. When used for treating stress incontinence, or irritable bowel syndrome, a therapeutically amount will comprise the active ingredient in a quantity of from 0.1 to 15 mg per day, preferably 0.2 to 10 mg/day, generally administered as a single dose, or as needed. The active ingredient may be given once a day. Preferably, however, the active ingredient will be administered in smaller doses two or three or more times a day to maintain more consistent plasma levels.

The oxybutynin may be delivered in dry powder form, e.g. via a dry powder inhaler (DPI), metered dose inhaler (MDI), or dissolved in a suitable liquid for nebulization in a therapeutically effective unit dose delivery amount. For treating acute symptoms of respiratory distress, a dose of oxybutynin should be taken at the first sign of respiratory distress. For treatment of chronic respiratory distress, oxybutynin should be taken daily according to a regimen recommended by a physician. Similarly, treating symptoms of stress urinary incontinence, a dose of oxybutynin should be taken at the first sign of stress, or upon onset of the first sign of urgency or just prior to anticipated onset of stress, e.g. just before a patient is scheduled to talk in front of an audience. In a preferred embodiment of the invention, the dry powder oxybutynin is packaged for delivery in a piezo-electronic dry powder inhaler such as described in U.S. Pat. No. 6,026,809. The terms "fine drug particles," and "aerodynamic particle size" as used herein, mean particles having a size sufficiently small so as to be delivered to the airways of the lungs, and especially to the small airways. For optimal delivery to the lungs, the dry powder form of the therapeutic agents described herein preferably should be micronized, spray dried, or engineered to a maximum aerodynamic particle size in the range of 0.01 µm to 20 µm, from 0.25 µm to 5 µm, or from 0.5 µm to 4 µm.

As used herein, the term "agent for reversal of CR" is intended to encompass any agent that when administered at an effective level will increase the anti-inflammatory response induced by a corticosteroid. This term applies not only agents for reversal of CR, but any salt or derivative of said agent having activity to reverse CR, and which is non-toxic and pharmacologically acceptable.

As used herein, CR reversal agents, include but are not limited to, vitamin D, vitamin D analogs, synthetic vitamin D, vitamin D receptor agonists and antagonists, calcitol, theophylline and equivalents thereof. Also included are CR reversal agents known to those skilled in the art.

As used herein, the term "vitamin D" is intended to encompass vitamin D, vitamin D2, vitamin D3, vitamin D analogs, synthetic vitamin D, vitamin D receptor agonists and antagonists, calcitriol, calcitol and equivalents thereof.

As used herein, the term "vitamin A" is intended to encompass those agents that interact with Retinoic Acid Receptor (RAR) including but not limited ATRA, ATRA derivatives, RAR agonists, 13-cis Retinoic acid and RAR selective agonists for example, palovarotene.

As used herein, the term "alveolar growth agent" is intended to encompass any agent that promotes the growth of new alveoli via the retinoic acid receptor, and includes ATRA or RAR selective agent therapy.

As used herein, the term "alveolar maintenance agent" is intended to encompass any agent that when administered at an effective level will increase the anti-inflammatory response induced by COPD, COPDe and emphysema and any undesirable effects of ATRA or RAR selective agent therapy. This term applies not only to agents for alveolar maintenance, but any salt, hydrate, prodrug or derivative of said agent having similar activity, and which is non-toxic and pharmacologically acceptable.

As used herein, bronchodilating substances include, but are not limited to, beta2-agonists (short and long acting, LABA), long acting muscarinic antagonists (LAMA), anti-cholinergics (short acting), and theophylline (long acting). "Co-administered," as used herein, means to deliver more than one pharmaceutical or therapeutic agent, for example, both corticosteroid and agent for reversal of CR as an aerosol within the same breath via the pulmonary route.

"An effective amount," as used herein, is an amount of the pharmaceutical composition that is effective for achieving a desired therapeutic effect, including but not limited to bronchodilation, CR reversal, anti-inflammation, alveolar regrowth. For example, an effective amount of an agent for reversal of CR may comprise the specified amount of calcitriol, within a defined aerodynamic particle size range suitable for absorption in the lungs, that is able to reduce or eliminate the resistance to corticosteroids.

As used herein, "pharmaceutical" and "therapeutic" agents include but are not limited to any and all medicaments and pharmaceutical agents and formulations that may be administered for the treatment of pulmonary disease, including agents for preventing disease and including agents for maintaining improvement of disease condition. As used herein, such therapeutic and pharmaceutical agents include, but are not limited to, corticosteroids, muscarinic antagonists, macrolides, and non-steroidal anti-inflammatory drugs (NSAIDs), antioxidants, iNOS inhibitors, phosphoinositide-3-kinase-δ inhibitors, p38 MAP kinase inhibitors, JNK inhibitors, MIF inhibitors, p-glycoprotein inhibitors, macrolides, calcineurin inhibitors, and vitamin D, synthetic vitamin D, vitamin D analogs, calcitiol, vitamin A, All Trans Retinoic Acid (ATRA), retinoic acid receptor (RAR) agonists, RAR selective alveolar growth agents, budesonide, fluticasone, beclomethasone, flunisolide, triamcinolone, mometasone, ciclesonide, loteprednol, fluorometholone as well as any derivative, equivalent or pharmaceutically acceptable salt thereof.

A "pharmaceutical" or "therapeutic" composition as used herein, means a medicament for use in treating a patient, for example, an agent for reversal of CR in a dry powder form of a defined aerodynamic particle size prepared in a manner that is suitable for pulmonary administration to a patient. A pharmaceutical composition according to the invention may optionally, include a non-toxic pharmaceutically acceptable carrier. In certain embodiments "pharmaceutical" or "therapeutic" composition may comprise a singular entity (i.e. calcitriol alone), or a combination of compositions selected from the group consisting of CR reversal agents, anti-inflammatory agents, bronchodilators, alveolar growth agents, and others.

It should be emphasized that the above-described embodiments of the present device and process, particularly, and "preferred" embodiments, are merely possible examples of implementations and merely set forth for a clear understanding of the principles of the disclosure. All these and other such modifications and variations are intended to be included herein within the scope of this disclosure and protected by the following claims. Therefore the scope of the disclosure is not intended to be limited except as indicated in the appended claims.

The following specific examples will illustrate the invention as it applies to the methods of treatment using the inhaler. It will be appreciated that other examples, including minor variations in procedures will be apparent to those skilled in the art, and that the invention is not limited to these specific illustrated examples.

EXAMPLES

Example 1

Micronization of Oxybutynin

Oxybutynin in crystalline form is micronized to a median aerodynamic particle size of less than 10 microns. The powder is packaged in a dry powder inhaler (DPI) made in accordance with U.S. Pat. No. 6,026,809.

Example 2

Micronization of Oxybutynin Chloride

Example 1 was repeated, using micronized oxybutynin chloride of median aerodynamic particle size of less than 5 microns in place of oxybutynin.

Example 3

Preparation of Oxybutynin Xinafoate

Example 1 was repeated, using micronized oxybutynin xinafoate salt of maximum aerodynamic particle size of about 10 microns in place of oxybutynin. The oxybutynin xinafoate salt was prepared by as follows: A 250 mL, round-bottom flask was equipped with a magnetic stirrer, a thermocouple, and a nitrogen-inlet adapter. Under nitrogen, the flask was charged with oxybutynin (20.04 g, 0.056 mol.), xinafoic acid (10.69 g. 0.057 mol. 1.02 equiv, and methyl tert-butyl ether (100 mL, 5 vol). The solids dissolved almost immediately at approximately 18° C. The batch was warmed to 50° C., and at approximately 21° C., crystallization started. The mixture was maintained at 50° C. for one hour, was cooled to 33° C. in air, and then in an ice bath to 3° C. The mixture was maintained at <5° C. for one hour and was filtered, and the filter cake was washed with methyl tert-butyl ether (100 mL). The wet cake was dried in a vacuum oven at 45° C. for one hour.

Figure 5:
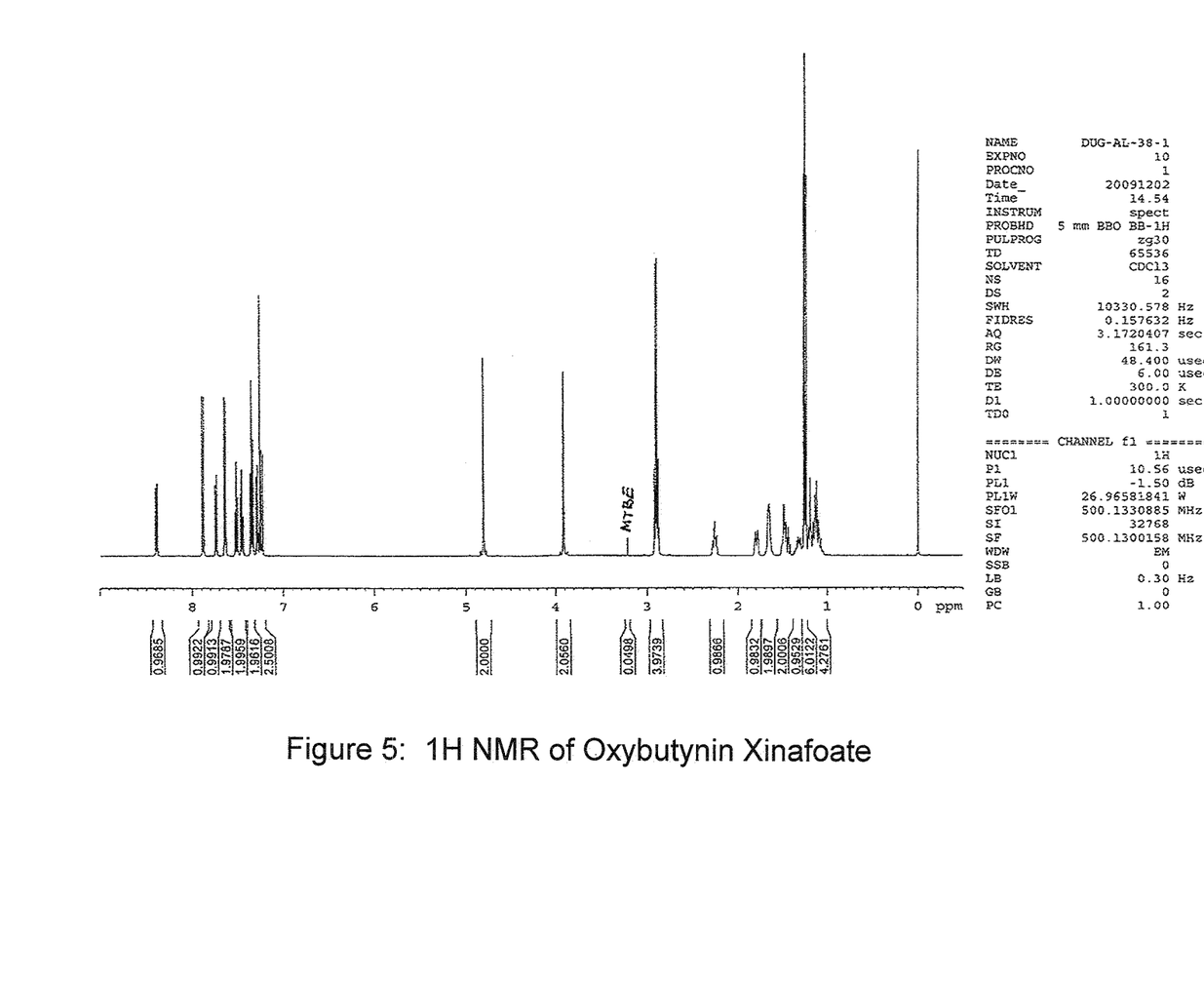
FIGS. 5 and 6 provide 1H NMR and FT-IR structure analysis.
Figure 6:
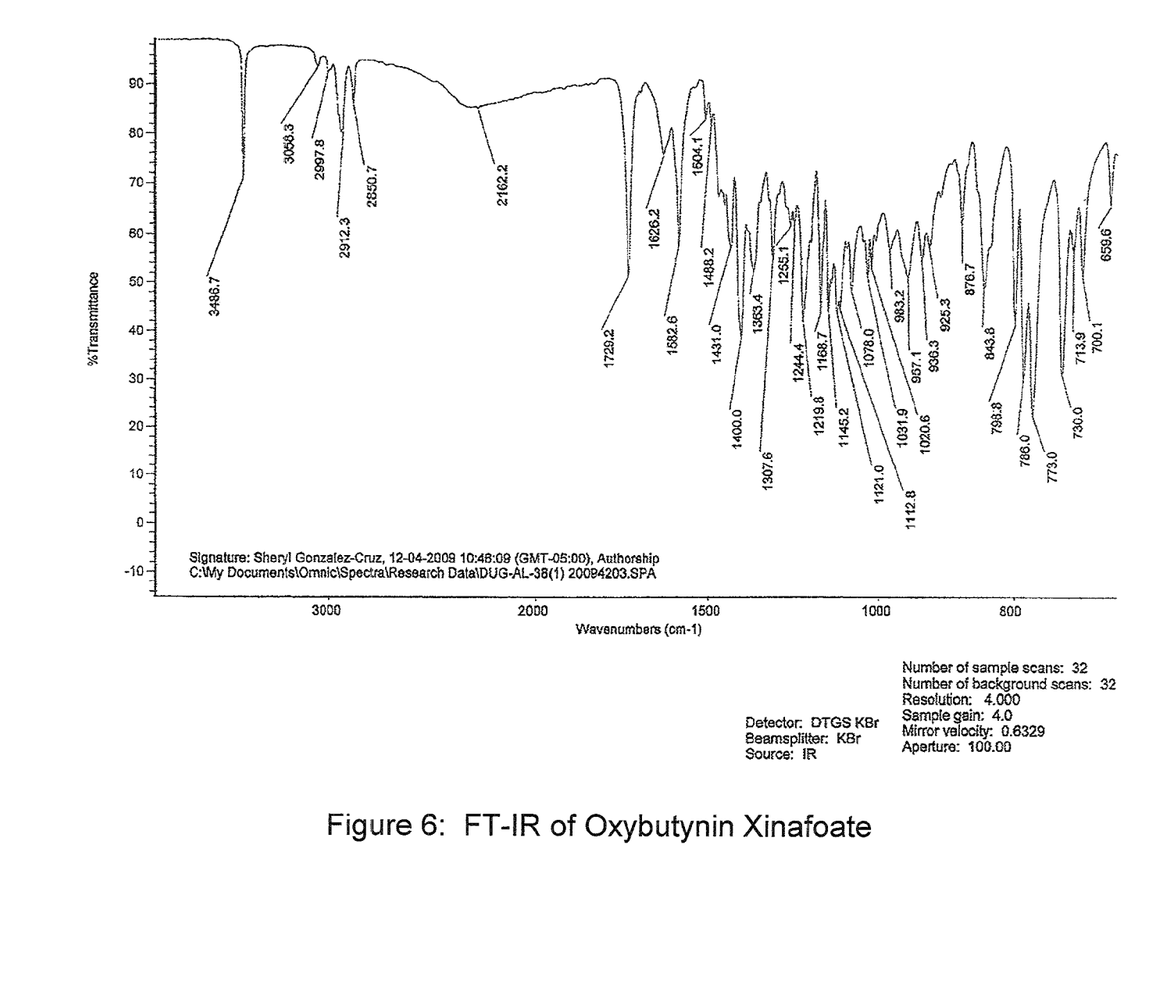
Figure 7:
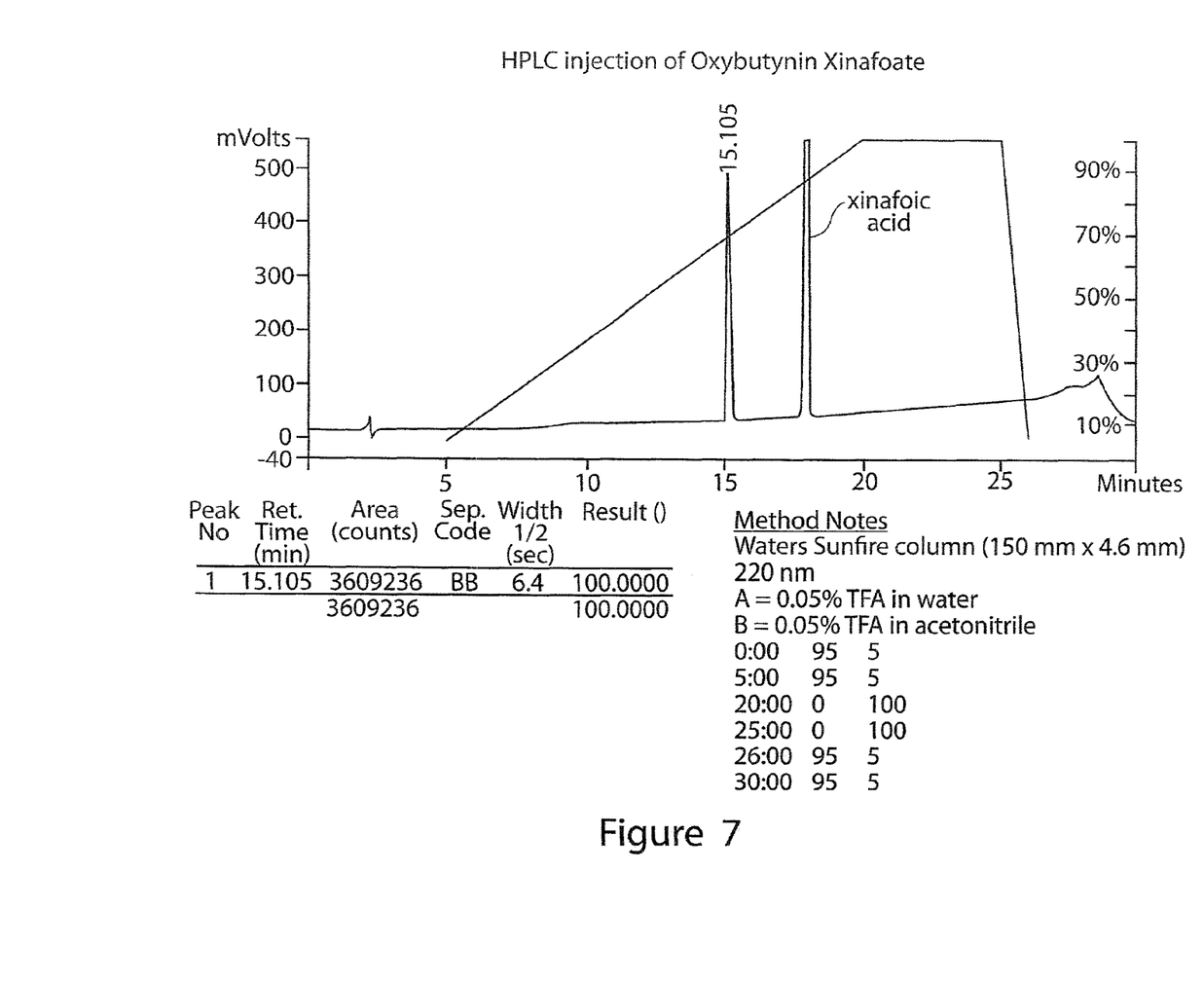
FIG. 7 provides HPLC analysis.
Figure 8:
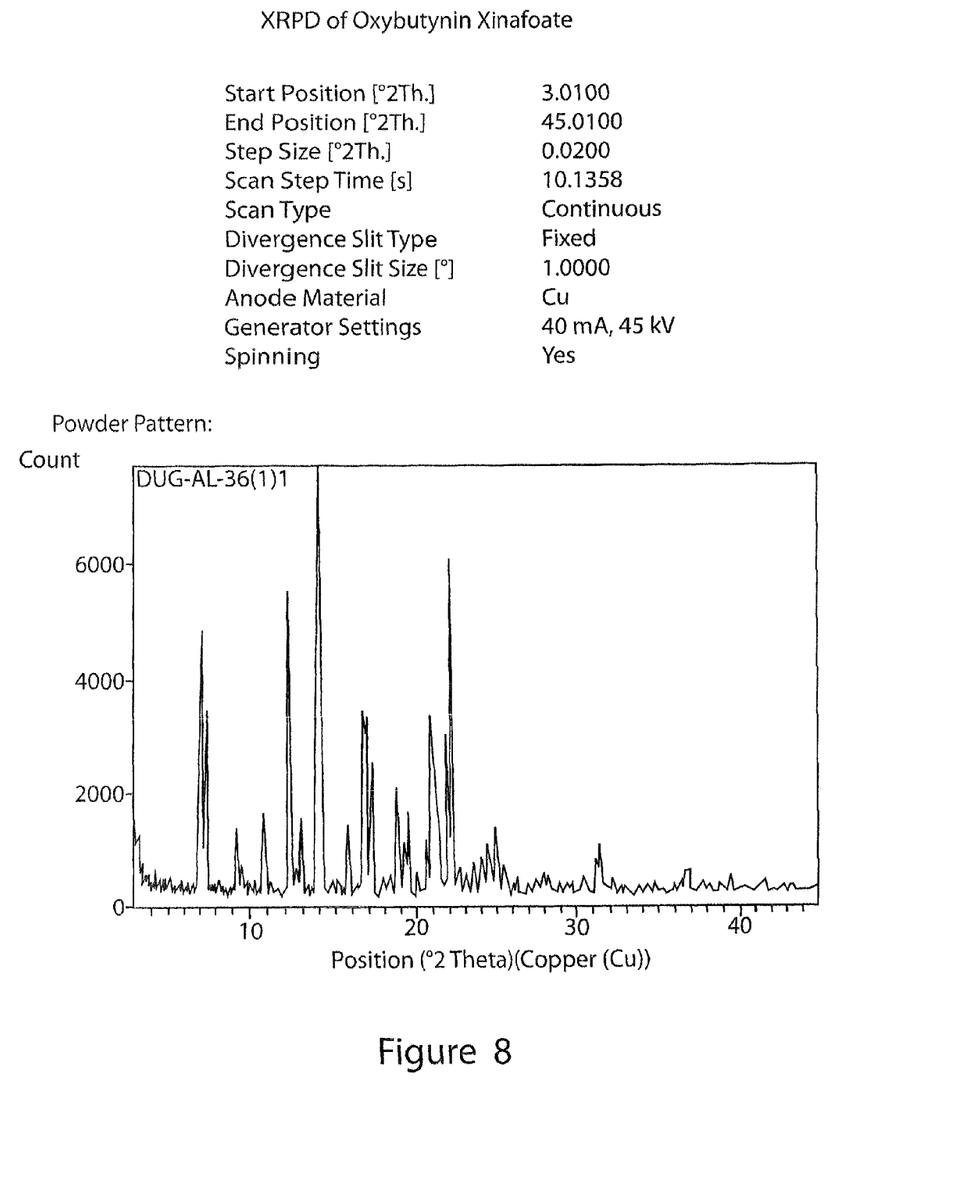
FIGS. 8 and 9 provide crystallinity, compound purity, and melting point determined by XRPD and DSC.
Figure 9:
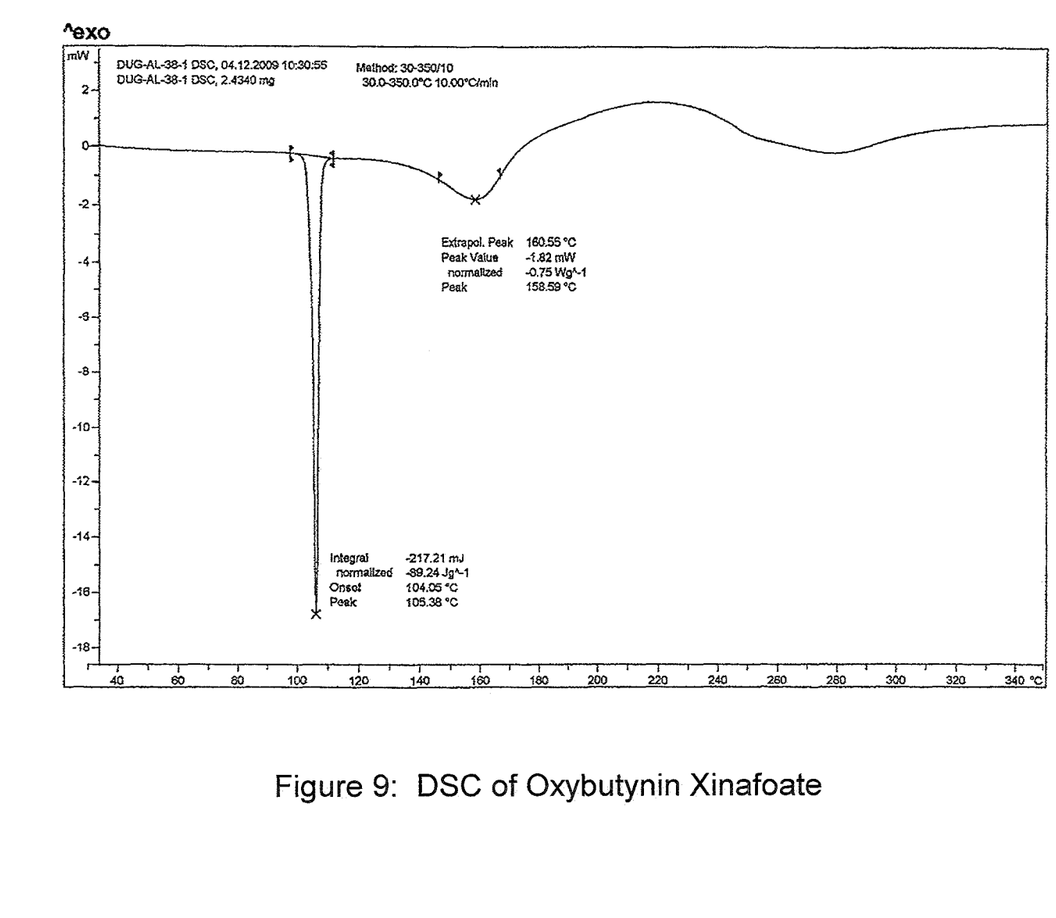

After salt synthesis, structure was confirmed by 1H NMR and FT-IR (FIGS. 5 and 6). HPLC analysis confirmed >99% potency through quantification of AUC at 15.1 min (FIG. 7). Crystallinity, compound purity, and melting point were also determined by XRPD and DSC (FIGS. 8 and 9). Both tests indicated a highly crystalline substance (DSC detected no cold crystallization) with a melting point of 105° C. Water content was determined to be 0.057% by KF titration.

Example 4

Comparative Effects of Bronchodilators

Figure 2:
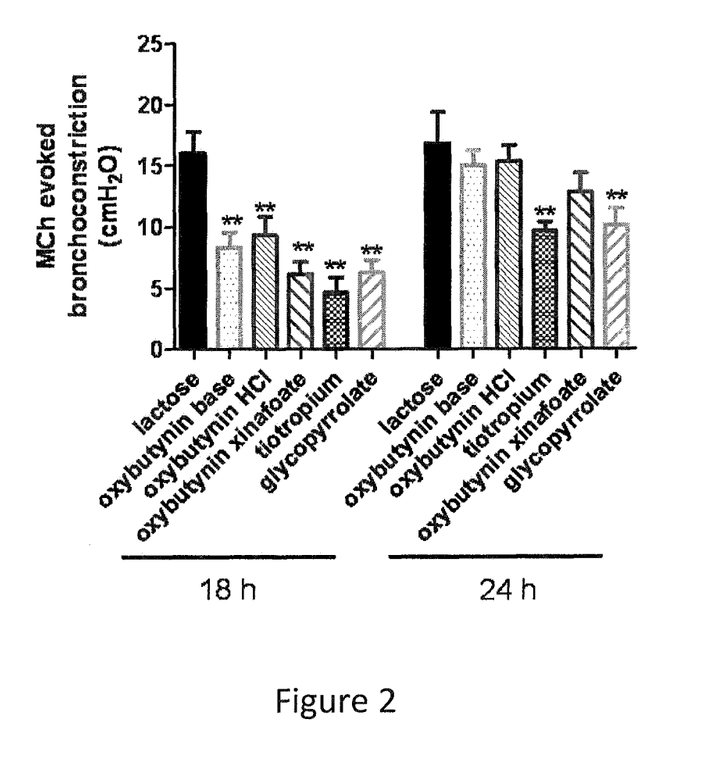
FIG. 2 compares inhibition of methacholine induced bronchoconstriction by oxybutynin, oxybutynin salts, tiotropium and glycopyrrolate at 18 hours and 24 hours. More particularly, FIG. 2 plots a comparison of the bronchoconstriction evoked by methacholine (MCh, 10 μg/kg, i.v.) 18, and 24 h after lactose (2 mg, i.t., n=6), oxybutynin base 2 mg, i.t., n=6), oxybutynin HCl (2.5 mg, i.t., n=6), oxybutynin xinafoate 3 mg, i.t., n=6), tiotropium (1 mg/kg, i.t., n=6) or glycopyrrolate (1 mg/kg, i.t., n=6) administration. Each bar represents the mean value and the vertical lines show s.e. mean. Changes in bronchoconstriction for oxybutynin or tiotropium treated animals (anaesthetized guinea pigs) were compared the time matched lactose control animals using ANOVA followed by Dunnetts test. ** P<0.01.

Example 1 was repeated, using micronized oxybutynin base, oxybutynin hydrochloride salt, and oxybutynin xinafoate salt of maximum aerodynamic particle size of about 10 microns in place of oxybutynin. The level of bronchodilator activity of oxybutynin was compared to Tiotropium and Glycopyrrolate 18 and 24 hours after administration in anaesthetized guinea pigs. FIGS. 1 and 2 shows comparative effects of pulmonary delivery of oxybutynin on anaesthetized guinea pigs.

Example 5

Comparative Effects of Bronchodilators: Oxybutynin Xinofoate and Others

Figure 3:
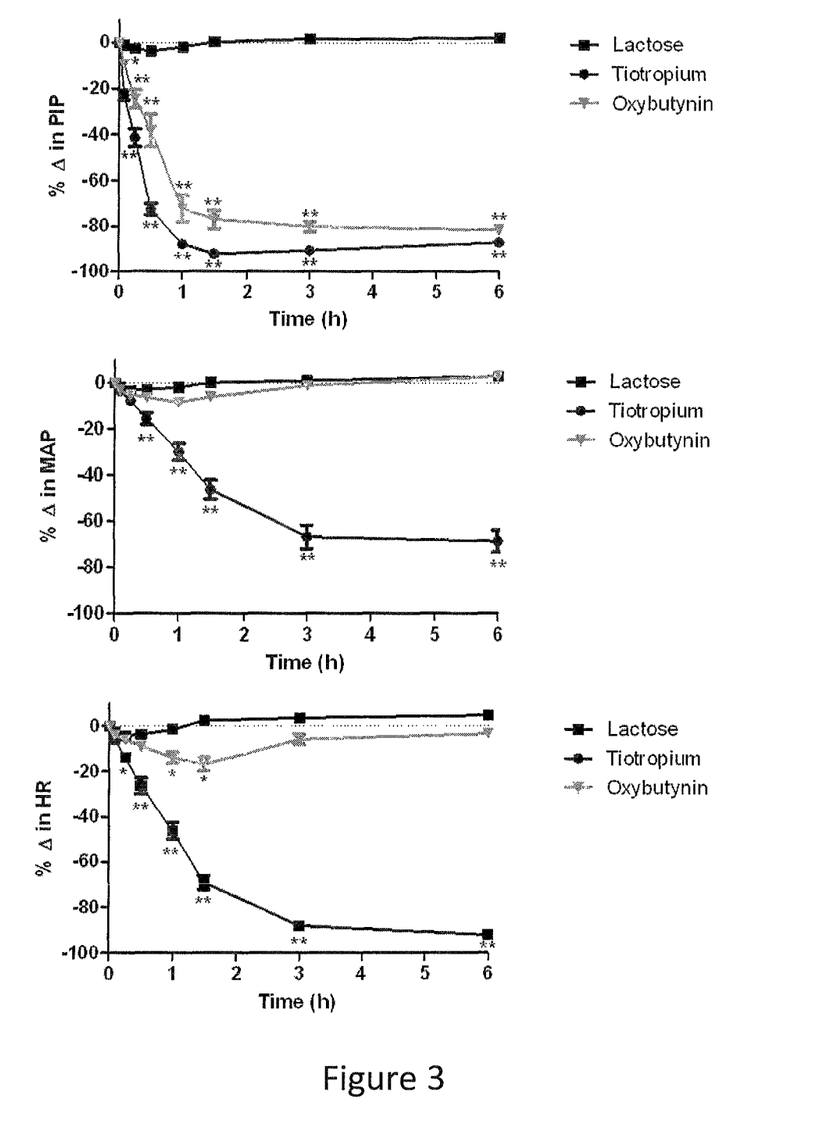
FIG. 3 is a series of graphs comparing changes from control response evoked by methacholine over time by oxybutynin xinafoate and tiotropium in pulmonary inflation pressure, mean arterial blood pressure and heart rate. More particularly, FIG. 3 plots a comparison of the changes from the control response evoked by methacholine (10 μg kg$^{-1}$, i.v.) over time (h) in the presence of lactose (i.t., n=6), oxybutynin xinafoate (7.5% w/w, i.t., n=6), or tiotropium (1 mg, i.t., n=6) in pulmonary inflation pressure (PIP) mean arterial blood pressure (MAP) and heart rate (HR). Each point represents the mean value and the vertical bars show s.e. mean. Percentage changes in oxybutynin or tiotropium treated animals were compared to the respective lactose control animals (anaesthetized guinea pigs) using ANOVA followed by Dunnetts test. * P<0.05, ** P<0.01.

Example 1 was repeated, using micronized oxybutynin xinafoate salt of maximum aerodynamic particle size of about 10 microns in place of oxybutynin. The onset of action and resulting systemic levels of oxybutynin xinafoate was compared to Tiotropium for the first 6 hours after administration in anesthetized guinea pigs. FIG. 3 compares effects of pulmonary delivery of oxybutynin to Tiotropium on anaesthetized guinea pigs in the initial 6 hours after administration. Oxybutynin showed similar protection against methacholine induced airway constriction as Tiotropium; however, did not have as significant an influence on cardiovascular conditions.

Figure 4:
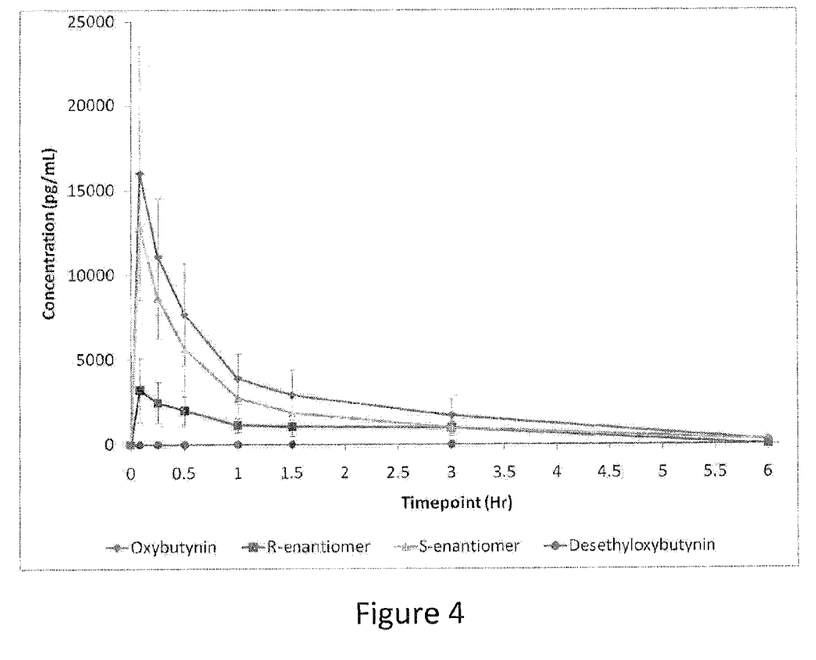
FIG. 4 shows pharmacokinetics of pulmonary administration of oxybutynin over time. More particularly, FIG. 4 plots anaesthetized guinea pig (n=5) pharmacokinetic profile of Oxybutynin, Oxybutynin enatiomers, and major metabolite (desethyloxybutynin) following dry powder insufflation.

FIG. 4 shows the resulting pharmacokinetics of pulmonary administration of oxybutynin. Systemic levels of DEO resulting from pulmonary delivery were below the LOQ of the detection method and much lower than clinically relevant levels.

Changes may be made without departing from the spirit and scope of the above-described invention. For example, the oxybutynin may be co-administered with other compounds or agents for reducing adverse side effects or to treat the side effect. For example, cholinergic agonists such as described in PCT US09/034018 may be co-administered with the oxybutynin to reduce the effect of dry mouth.

CONCLUSION

Delivery of micronized particles of oxybutynin directly to the lungs, as needed, could be found to provide relief to patients suffering from respiratory diseases such as asthma and COPD, and also from urge urinary incontinence and symptoms of stress urinary incontinence and irritable bowel syndrome.

In a guinea pig model of bronchoconstriction, oxybutynin was found to have a significantly bronchoprotective effect from 0.25 to 24 hours without a prolonged significant effect on arterial pressure and heart rate.

Pulmonary administration of oxybutynin also avoids significant formation of the first-pass primary metabolite DEO and thus significantly reduces adverse side effects which traditionally have been associated with administration of oxybutynin via oral or transdermal delivery. Additionally, dosage amounts of oxybutynin administered via pulmonary delivery route are significantly lower than dosage amounts of oxybutynin when delivered via oral or transdermal delivery routes. Furthermore, pulmonary delivery of oxybutynin results in prolonged therapeutic levels in the lungs which would permit once or twice daily dosing compared to oral delivery of oxybutynin which typically is administered three times daily.

While the invention has been described in detail herein in accordance with certain preferred embodiments thereof, many modifications and changes therein may be affected by those skilled in the art. Accordingly, it is intended that the appended claims cover all such modifications and changes as may fall within the spirit and scope of the invention.

We claim:

1. A method for treating pulmonary disease comprising delivering directly to a patient's lungs a therapeutically effective amount of a salt form of oxybutynin in combination with one or more pharmaceutically effective agents, wherein the salt form of oxybutynin is selected from the group consisting of a xinafoate salt and a laurate salt, and wherein, the oxybutynin and the pharmaceutically effective agents are delivered in dry powder form using a dry powder inhaler, wherein the dosage of the therapeutically effective amount of oxybutynin is within the range of 0.001 to 20 mg per day, 0.02 to 15 mg per day, or 0.05 to 10 mg per day administered as needed.

2. The method according to claim 1, wherein oxybutynin comprises oxybutynin xinafoate.

3. The method of claim 1, wherein the pulmonary disease comprises asthma, atelectasis, bronchitis, chronic obstructive pulmonary disease, emphysema, lung cancer, pneumonia or pulmonary edema.

4. The method according to claim 1, wherein the dry powder inhaler includes a piezo vibrator.

5. The method according to claim 1, wherein oxybutynin is delivered in dry powder form having a mass median aerodynamic particle size selected from the group consisting of 0.5-20 microns, 0.5-15 microns, 0.5-10 microns, or 0.5-5 microns.

6. A method for treating chronic obstructive pulmonary disease comprising delivering directly to a patient's lungs a therapeutically effective amount of a salt form of oxybutynin in combination with one or more pharmaceutically effective agents, wherein the salt form of oxybutynin is selected from the group consisting of a xinafoate salt and a laurate salt, and wherein, the oxybutynin and the pharmaceutically effective agents are delivered in dry powder form using a dry powder inhaler.

* * * * *